United States Patent [19]

Valenta

[11] Patent Number: 5,321,261
[45] Date of Patent: Jun. 14, 1994

[54] NORMALIZATION TECHNIQUE FOR PHOTON-COUNTING LUMINOMETER

[75] Inventor: Robert J. Valenta, West Chicago, Ill.

[73] Assignee: Packard Instrument Company, Inc., Downers Grove, Ill.

[21] Appl. No.: 943,398

[22] Filed: Sep. 10, 1992

[51] Int. Cl.$^5$ .............................................. G01N 21/76
[52] U.S. Cl. .................. 250/252.1; 250/328; 250/361 C
[58] Field of Search ............... 250/252.1 R, 328, 394, 250/366, 369, 363.09, 361 C

[56] References Cited

U.S. PATENT DOCUMENTS

| | | | |
|---|---|---|---|
| 3,833,827 | 9/1974 | Shaffer | 313/486 |
| 4,039,889 | 8/1977 | Vicai | 313/487 |
| 4,093,857 | 6/1978 | Lapidus | 250/369 |
| 4,588,897 | 5/1986 | Inbar et al. | 250/369 |
| 4,703,574 | 11/1987 | Garjian | 40/545 |

FOREIGN PATENT DOCUMENTS 4029083  1/1992  Japan ........................... 250/252.1 R

OTHER PUBLICATIONS

Mendenhall, "The Autoradioluminescence of Uranyl Salts", *Journal of Photochemistry & Photobiology*, A:-Chemistry, 52, (1992), pp. 285–302.

Hasting et al., "Total Quantum Flux of Isotropic Sources", *Journal of Optical Society of America*, (1963), vol. 53, #11, pp. 1410–1414.

Lee et al., "Quantum Yields of the Luminol Chemiluminescence Reaction in Aqueous and Aprotic Solvents", *Photochemistry and Photobiology*, (1972), vol. 15, pp. 227–237.

Bezman et al., "Construction and Calibration of an Apparatus for Absolute Measurement of Total Luminescence at Low Levels", (1991), *Analytical Chemistry*, vol. 43, No. 13, pp. 1749–1753.

Seliger, "Excited States and Absolute Calibrations in Bioluminescence", *Methods in Enzymology*, vol. LVII, pp. 560–601.

Seliger, "Single Photon Counting and Spectroscopy of Low Intensity Chemiluminescent Reactions", *Liquid Scintillation Counting Recent Applications & Development*, vol. II, (1980), Academic Press, pp. 281–319.

O'Kane et al., "Encapsulated Radiophosphorescent Standards for Day-to-Day Photometer Calibration", (1990), *Photochemistry and Photobiology*, vol. 52, No. 4, pp. 723–734.

Sale literature of Biolink Technology Ltd., "Luminescence Standards Light Test Standards Systems–Biolink", (no date).

*Primary Examiner*—Carolyn E. Fields
*Attorney, Agent, or Firm*—Arnold, White & Durkee

[57] ABSTRACT

A normalization system for multi-photodetector single photon counting luminescent measuring systems and a standard for use in the same. The method comprises calculating one or more counting ratios for each photodetector in the single photon counting system and multiplying counts of unknown samples by the inverse of the appropriate counting ratio. A counting ratio for a particular photodetector is calculated by dividing the count of a standard measured by the photodetector by the count of the same standard measured by a reference photodetector. The particular standard developed employs calcium tungstate:lead as a scintillator and tritium or carbon-14 thymidine as a means of exciting the scintillator. This standard has the advantages of providing a good model of typical luminescence chemistry and producing an emission pattern which is susceptible to single photon counting.

31 Claims, 3 Drawing Sheets

NORMALIZATION TECHNIQUE FOR PHOTON-COUNTING LUMINOMETER

FIELD OF THE INVENTION

The present invention generally relates to single-photon counting photodetector systems. More particularly, it pertains to a system for normalizing two or more photodetectors in a single photon counting luminescent measuring system and a standard for use in the same.

BACKGROUND OF THE INVENTION

With the advent of multiple detector, single-photon counting systems, a need has developed to normalize an array of photodetectors so that the measure of luminescence is independent of which photodetector performs the measurement.

Furthermore, in modelling chemiluminescent and bioluminescent emissions, it is generally desirable to use a standard with a peak wavelength approximately the same as that of the sample which is to be measured. While numerous radiophosphorescent standards have been developed to model low intensity emissions which are typical of chemiluminescent and bioluminescent samples, none have a decay constant long enough for single photon counting systems and a peak wavelength which matches that of the typical luminescence chemistry, e.g., approximately 430 nanometers.

SUMMARY OF THE INVENTION

An object of this invention is to normalize two or more photodetectors in single-photon counting luminescent measuring systems. Normalization in this application means compensating for differences in counting efficiencies between two or more photodetectors by adjusting the count of one photodetector so as to correspond to the count of another. In a multiple photodetector system, counting efficiency can vary from detector channel to detector channel due to variations in individual detector's sensitivities, optical geometry, and output pulse characteristics and variations in individual counting circuits' pulse detection thresholds and time resolution.

In accordance with the present invention, two or more photodetectors are normalized in a single-photon counting system by computing a counting ratio for each photodetector. More specifically, in a single-photon counting system with two or more photodetectors, one photodetector is designated as a reference. Each photodetector then measures a standard sample. A counting ratio is computed for each photodetector by dividing the count of that photodetector by the count of the reference photodetector. Subsequently, when measuring unknown samples, the count by a given photodetector is normalized by multiplying that count by the inverse of the photodetector's counting ratio.

In another embodiment, multiple standards with varying activity levels are utilized to compute multiple counting ratios for each photodetector. Each standard represents a range of activity levels. The activity level of standards may be varied by, for example, employing a different radioactive material or altering the geometry of the sample well. Subsequently, when a sample is measured, the resulting count is normalized by multiplying by the inverse of the measuring photodetector's counting ratio which corresponds to the sample's activity level. Alternatively, counts of multiple standards with varying activity levels can be utilized to extrapolate counts of other activity levels and corresponding counting ratios. Another alternative would be to compute a single counting ratio based on the average of several counting ratios computed for varying activity levels.

The present invention also provides a scintillator with a decay constant of about 12 μs, which is long enough for use in single photon counting systems, and a peak wavelength of about 433 nanometers. More particularly, the present invention employs calcium tungstate:lead ($CaWO_4$:Pb or $CaWO_4$:[W]:Pb, where [] represents a complex ion activator group) as a scintillator. Tritium or carbon-14 thymidine is used to excite this phosphor. This standard provides an improved model of typical luminescence chemistry.

BRIEF DESCRIPTION OF THE DRAWINGS

Other objects and advantages of the invention will become apparent upon reading the following detailed description and upon reference to the drawings in which.

Figure 1:
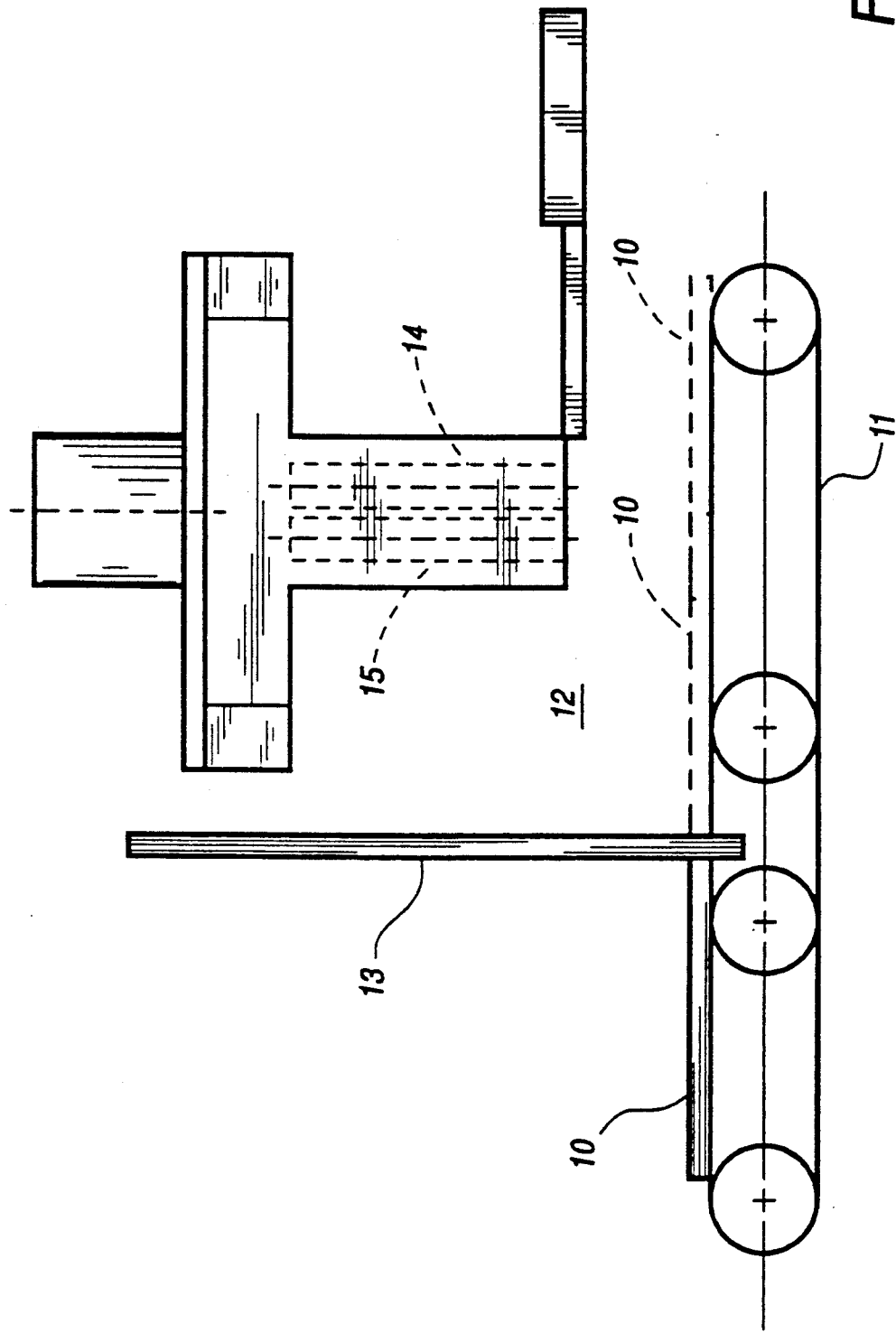
FIG. 1 is a diagrammatic side elevation of a multi-photodetector single photon counting system for measuring the luminescence of samples in a 96-well plate.

While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE PREFERRED EMBODIMENT

Turning now to the drawings and referring first to FIG. 1, there is shown a scintillation spectrometer for measuring the luminescence of multiple samples contained in a sample microplate 10. The microplate 10 is loaded by a conveyor 11 into a light-tight counting chamber 12 via a conventional shutter mechanism 13 which is opened and closed to permit ingress and egress of successive sample plates. Within the counting chamber, the multi-well microplate 10 is indexed beneath two rows 14 and 15 of photomultiplier tubes (PMTs).

Figure 2:
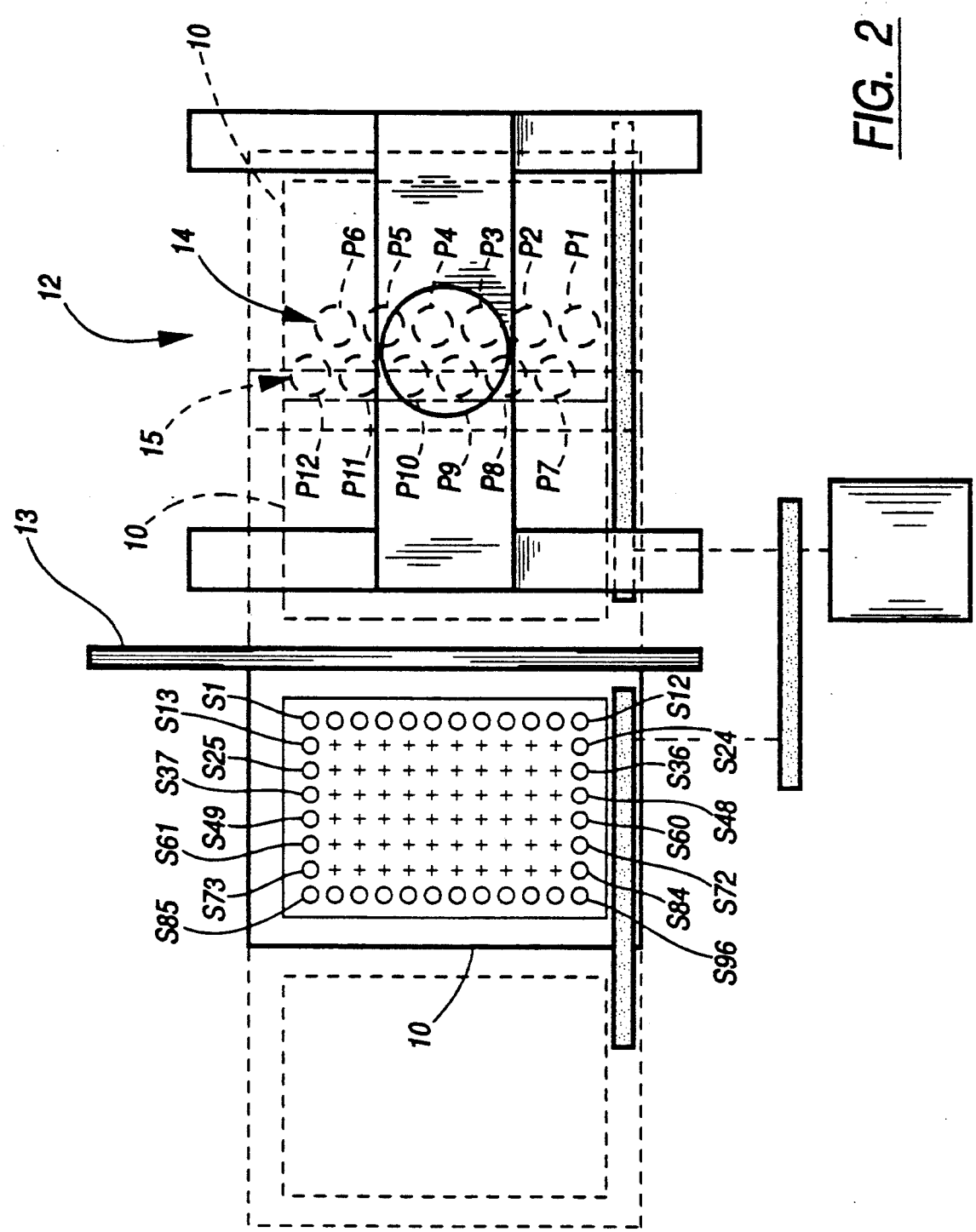
FIG. 2 is a diagrammatic top plan view of the system shown in FIG. 1.

In the particular embodiment illustrated in FIG. 2, the PMTs P are arranged in two rows 14 and 15, each containing six PMTs, for counting samples in the 96-well plate 10 forming an 8×12 matrix of sample wells S1-S96. The two rows of PMTs P1-P6 and P7-P12 are staggered relative to each other so that the PMTs in one row are aligned with alternate wells in one of the twelve-well rows, while the PMTs in the other row are aligned with the intervening wells in an adjacent twelve-well row. Consequently, after any given twelve-well row has been passed under both rows of PMTs P1–P6 and P7–P12, the samples in all twelve wells in that row will have been counted.

The PMTs produce electrical output signals corresponding to the detected optical events of the wells they are adjacent to, and this signal is processed electronically to determine the amount of luminescence of the corresponding sample.

Figure 3:
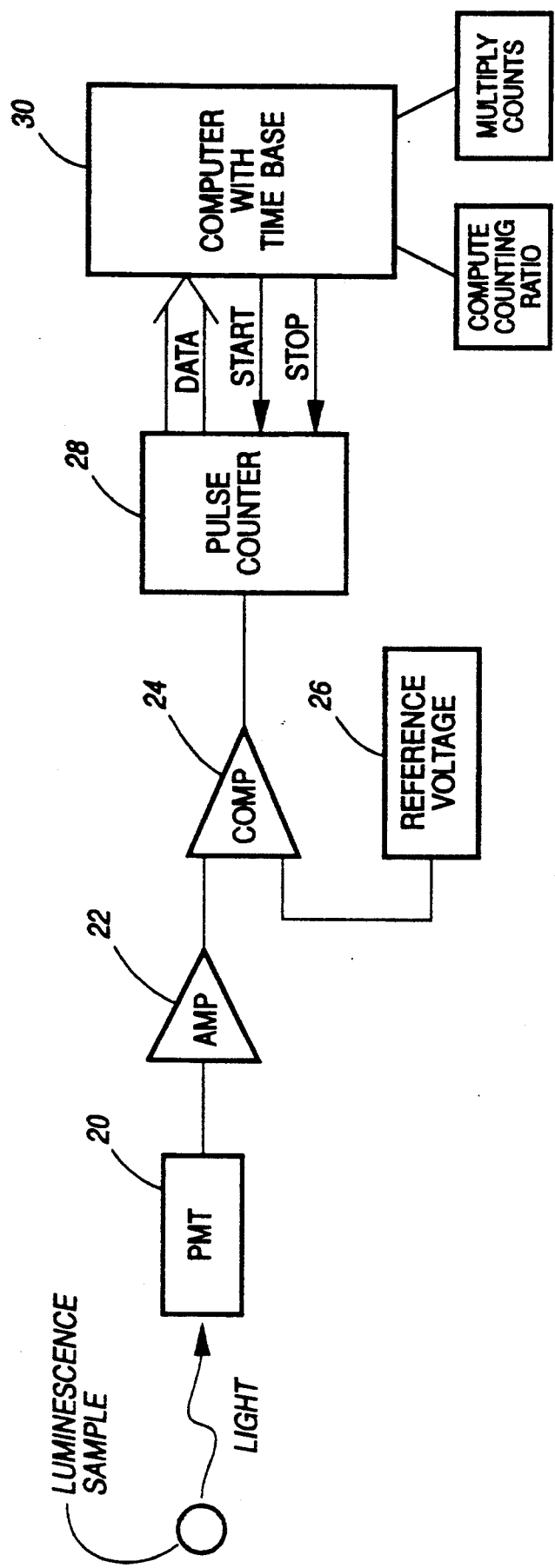
FIG. 3 is a block diagram of the electronic signal processing system associated with each of the photomultiplier tubes used in the system of FIGS. 1 AND 2.

As illustrated in FIG. 3, the output of each of the twelve PMTs 20 is passed through an amplifier 22 to a comparator 24 which serves as a single photoelectron pulse detector. More specifically, the comparator 24 receives a reference voltage from a single-photon threshold reference source 26, and produces an output pulse only when the input signal from the PMT exceeds the threshold set by the reference voltage. These output pulses from the comparator 24, sometimes referred to as "singles" pulses, indicate that the amplitude of the detected pulse is large enough to represent at least a single photoelectron. The output pulses from the comparator 24 are fed to a pulse counter 28, which functions to sum the "singles" pulses received from the comparator. The counter 28 sums the received pulses during a time interval set by a computer 30 with a time base. The sum or count is then stored by the computer 30.

With the advent of single photon counting systems using two or more photodetectors, there is a need for the normalization of the individual photodetectors so that variances in counting efficiencies among the photodetectors can be offset. The present invention compensates for the variances in counting efficiencies of the multiple photodetectors so that the resulting photon emission count for a given sample is independent of which photodetector performs the measurement.

With the present invention, a standard sample of photon emitting material is employed to normalize multiple photodetectors. The standard sample emits a steady stream of photons at a relatively slow rate so that the photodetectors are able to resolve individual photons. Each photodetector then counts the photons emitted by the standard sample. The count of one of the photodetectors is used as a reference and is divided into the counts of the other photodetectors. The resulting ratio for each photodetector can then be divided into the counts of subsequent measurements of unknown samples from that same photodetector. In this way variances in counting efficiencies among the multiple photodetectors can be offset.

One manner of performing the normalization process is as follows, referring again to FIG. 2. A standard sample is placed in a well of the microplate, for example well S6. One PMT is designated a reference photodetector, for example PMT P1. Note in the preferred embodiment of the single photon counting system the microplate 10 is capable of movement left and right along the x-axis by the conveyor 11 whereas the PMTs P1–P12 are capable of movement along the y-axis. This permits any of the twelve PMTs to be positioned over a given microplate well such as S6. As counting efficiency can be significantly affected by inaccurate positioning of a photodetector over a sample well, it is important that some form of reliable positioning technique is used. For example, locating pins may be attached to the bottom of the microplate 10 or the microplate 10 may be made with precise dimensions so as to permit positional reliance on the microplate's edges.

During normalization the PMT P1 is positioned over the well S6, and a count of photons emitted over a given time period is taken. Subsequently, one or more other PMTs are positioned over S6 and perform a count for the same time period. A counting ratio is then computed for each of these other PMTs by dividing each of their respective counts by the count of the reference PMT. For example, if the count produced by the reference PMT P1 is 100 and the count by the PMT P2 is 95, the counting ratio for the PMT P1 is 1.0 and that of the PMT P2 is 0.95.

During subsequent measurement of unknown samples, the counting ratio for each PMT is utilized to adjust for variances in counting efficiencies. This is achieved by dividing the actual count of a PMT by its counting ratio to produce a final count. For example, an actual count of 95 from the PMT P2 is adjusted by dividing that actual count by the counting ratio of 0.95. The resulting compensated count is 100. This is the count which would be expected if the PMT P1 had performed the counting.

In an alternative embodiment, a set of standards with varying activity levels are employed. These multiple standards are used either to calculate multiple counting ratios for each PMT corresponding to varying activity levels or to calculate an average counting ratio for each PMT. For example, four standards with varying activity levels can be contained in four different microplate wells, e.g., S6, S18, S30, and S42. One manner of varying the activity level of a standard is to use different radioactive materials. Another method of varying activity level is by altering the geometry of the microplate wells, for example by placing a hollow cylinder within the well. Counts are made of each of the four standards by the reference PMT P1 and one or more other PMTs, e.g., P2. Four counting ratios for each PMT are then computed. When measuring unknown samples, the counting ratio for the activity level closest to that of the sample is used to adjust the count of the measuring PMT. Alternatively, counting ratios for additional activity levels can be computed by extrapolation from the data obtained from the multiple standards. For example, a curve fitting of counting ratios versus activity level for each PMT can be performed, and then the resulting equation can be employed to determine the appropriate counting ratio for any activity level.

Another alternative is to calculate a single counting ratio for each PMT based on the average of the counting ratios for several activity levels. This method can be useful if the counting ratios do not vary significantly with activity levels.

The preferred standard for use in the present invention utilizes radioactive material and a scintillator to model the luminescence of chemiluminescent samples. The low level of energy of typical chemiluminescent samples makes the use of traditional photodetection measurement systems, which employ integration techniques, subject to inaccurate readings. The use of single photon counting photodetection measurement systems overcomes the disadvantages associated with low energy emissions. The preferred standard emits a continuous stream of photons at a slow enough rate that the photodetector is capable of counting the reception of individual photons. In particular, the preferred scintillator, Sylvania 2402 ($CaWO_4$:[W]:Pb, where [] represents a complex ion activator group) available from GTE, is a good model of typical chemiluminescent emissions in that it has a light output peak wavelength (433 nm) close to that of typical chemiluminescent emissions (430 nm) and a sufficiently long decay constant (12 $\mu s$) to permit the counting of individual photons. This scintillator is excited by either tritium or carbon-14. The manner of packaging the standard within the wells of a microplate has the further advantages of making the normalization plate both simple to employ and relatively safe. This packaging technique employs a potting material which maintains the phosphor and radioactive material within the microplate wells while protecting the user from unsafe levels of radioactive emissions.

Figure 4:
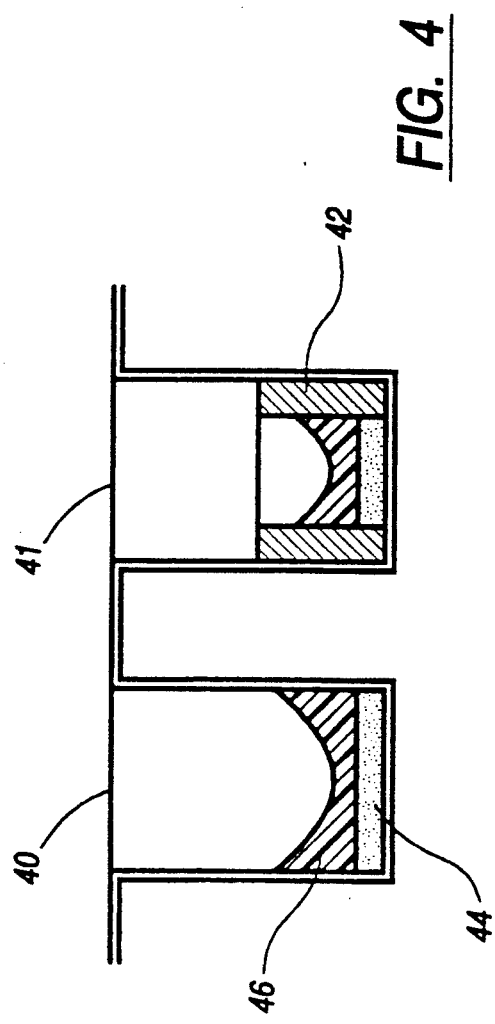
FIG. 4 is a sectional view of two microplate wells containing a radiophosphorescent standard.

FIG. 4 shows an embodiment of a preferred standard within microplate wells 40 and 41. Well 41 is a typical microplate well with a hollow aluminum cylinder 42 inserted so as to restrict the volume of the well. Use of the hollow cylinder 42 is one means of altering activity level. A mixture 44 of a scintillator, a binding material, and a radioactive material is located at the bottom of wells 40 and 41. A potting material 46 seals the mixture 44 in the wells. The mixture 44 is formed by placing an aqueous slurry of a scintillator and a binding material in the bottom of a well and then evaporating the water contained in the slurry. Next droplets of liquid radioactive material are added so that the radioactive material soaks into the scintillator/binder mixture. In a preferred embodiment, the scintillator comprises calcium tungstate:lead (CaWO$_4$:Pb or CaWO$_4$:[W]:Pb, where [] represents a complex ion activator group). Tritium or carbon-14 thymidine is used to excite this phosphor. This standard has a peak light output wavelength of 433 nanometers as compared to 430 nanometers for typical luminescent chemistry. Additionally, it has a decay constant of 12 $\mu$s which is well suited for use in single photon counting systems. Moreover, while photon emission is random, this standard yields on average a steady stream of photon emission, i.e., the number of photons per second is a constant.

Examples of suitable binding materials are carboxy methyl cellulose, vinyl acetate polymers, and calcium sulfate monohydrate. Preferred potting materials transmit light at the scintillator's peak output wavelength, here about 433 nm. Examples of suitable potting materials are epoxy and styrene.

I claim:

1. A method for normalizing two or more photodetectors in a single-photon counting system for measuring the luminescence of multiple samples, said photodetectors comprising a reference detector and one or more other photodetectors, said method comprising:
   successively counting the photon emissions of a standard by two or more photodetectors, at least one of said photodetectors being the reference detector;
   computing a counting ratio for each of said one or more other photodetectors, said counting ratio being defined as the ratio of counts from the corresponding one or more other photodetectors to the counts from the reference detector; and
   in subsequent use of the photodetection system, multiplying the counts of a luminescent sample measured by a particular photodetector by the inverse of said counting ratio computed for that particular photodetector.

2. The method of claim 1 wherein the photodetectors are photomultiplier tubes.

3. The method of claim 2 wherein the sample is chemiluminescent.

4. The method of claim 1 wherein the standard comprises:
   a scintillator with a peak wavelength approximately the same as that of said luminescent sample and a long decay constant,
   one or more radioactive materials,
   and a containment means.

5. The method of claim 4 wherein said scintillator has a decay constant greater than about 10 $\mu$s.

6. The method of claim 5 wherein said scintillator comprises calcium tungstate:lead.

7. The method of claim 4 wherein the standard additionally comprises a means for maintaining said scintillator and said one or more radioactive materials in said containment means.

8. The method of claim 7 wherein said means for maintaining said scintillator and said one or more radioactive materials in said containment means includes a binder material.

9. The method of claim 8 wherein said binder material is carboxy methyl cellulose.

10. The method of claim 7 wherein said means for maintaining said scintillator and said one or more radioactive materials in said containment means includes a potting material.

11. The method of claim 7 wherein said means for maintaining said scintillator and said one or more radioactive materials in said containment means includes a binder material and a potting material.

12. The method of claim 11 wherein said scintillator comprises calcium tungstate:lead and said one or more radioactive materials is either tritium or carbon-14 thymidine.

13. The method of claim 4 wherein said one or more radioactive materials is either tritium or carbon-14 thymidine.

14. A method for normalizing two or more photodetectors in a single-photon counting system for measuring the luminescence of multiple samples, said method comprising:
   successively counting the photons emitted by a standard by each of said photodetectors;
   computing a ratio of the count produced by each of said photodetectors and the count produced by one of said photodetectors selected as a reference, so that multiplying any subsequent measurement of luminescence by the inverse of the counting ratios computed for the respective photodetectors makes the measurement independent of the photodetector performing the counting.

15. A method for normalizing two or more photodetectors in a single-photon counting system for measuring the luminescence of multiple samples, said photodetectors comprising a reference detector and one or more other photodetectors, said method comprising:
   successively counting the photon emissions of two or more standards with varying activity levels by two or more photodetectors, at least one of said photodetectors being the reference detector;
   computing one or more counting ratios for each of said one or more other photodetectors, said one or more counting ratios being defined as the ratio of counts from the corresponding one or more other photodetectors of a standard to the counts from the reference detector of the same standard; and
   in subsequent use of the photodetection system, multiplying the counts of a luminescent sample measured by a particular photodetector by the inverse of one of said one or more counting ratios computed for that particular photodetector, said one of said one or more counting ratios constituting a photodetector's corresponding counting ratio.

16. The method of claim 15 wherein an average counting ratio for each of said one or more other photodetectors is computed from counts of said two or more standards with varying activity levels by each of said one or more other photodetectors, and wherein said average counting ratio for each of said one or more other photodetectors constitutes each photodetector's said corresponding counting ratio.

17. The method of claim 15 wherein a multitude of counting ratios for each of said one or more other photodetectors are computed from counts of said two or more standards with varying activity levels by each of said one or more other photodetectors, said multitude of counting ratios corresponding to the varying activity levels of the standards measured, and wherein in subsequent use of the photodetection system, a photodetector's corresponding counting ratio is chosen based on the activity level of the sample being measured from the set of said multitude of counting ratios for each of said one or more other photodetectors.

18. The method of claim 17 wherein the counting ratio chosen as a photodetector's corresponding counting ratio is the counting ratio for the photodetector calculated from the measurement of the standard with an activity level closest to that of the sample being measured.

19. The method of claim 17 wherein for each of said one or more photodetectors a counting ratio-activity level equation is derived from the data obtained by the counting of the two or more standards with varying activity levels, and wherein the counting ratio chosen as a photodetector's corresponding counting ratio is the counting ratio for the photodetector calculated from that photodetector's counting ratio-activity level equation based on the activity level of the sample being measured.

20. An apparatus for normalizing two or more photodetectors in a single-photon counting system for measuring the luminescence of multiple samples, said photodetectors comprising a reference detector and one or more other photodetectors, said apparatus comprising:

means for successively counting the photon emissions of a standard by two or more photodetectors, at least one of said photodetectors being the reference detector;

means for computing a counting ratio for each of said one or more other photodetectors, said counting ratio being defined as the ratio of counts from the corresponding one or more other photodetectors to the counts from the reference detector; and means for multiplying the counts of a luminescent sample subsequently measured by a particular photodetector by the inverse of said counting ratio computed for that particular photodetector.

21. The apparatus of claim 20 wherein the photodetectors are photomultiplier tubes.

22. The apparatus of claim 20 wherein the standard comprises:

a scintillator with a peak wavelength approximately the same as that of said luminescent sample and a long decay constant, one or more radioactive materials, and a containment means.

23. The apparatus of claim 22 wherein said scintillator comprises calcium tungstate:lead.

24. A standard for normalizing two or more photodetectors in a single-photon counting system used to measure the luminescence of samples, said standard comprising:

a scintillator whose photon emission has a peak wavelength of about 433 nanometers, a radioactive material whose radioactive decay excites photon emission from the scintillator, and containment means.

25. The standard of claim 24 wherein said radioactive material is either tritium or carbon-14 thymidine.

26. A standard for normalizing two or more photodetectors in a single-photon counting system used to measure the luminescence of samples, said standard comprising:

a scintillator whose photon emission has a peak wavelength of about 433 nanometers, means for exciting said scintillator, and a microplate.

27. A standard for normalizing two or more photodetectors in a single-photon counting system used to measure the luminescence of samples, said standard comprising:

a scintillator whose photon emission has a peak wavelength of about 433 nanometers, means for exciting said scintillator, containment means, and means for maintaining said scintillator in said containment means, said maintaining means including a binding material composed of carboxy methyl cellulose.

28. A standard for normalizing two or more photodetectors in a single-photon counting system to measure the luminescence of samples, said standard comprising:

a scintillator whose photon emission has a peak wavelength of about 433 nanometers, means for exciting said scintillator, containment means, and means for maintaining said scintillator and said means for exciting said scintillator in said containment means, said maintaining means including a potting material.

29. The standard of claim 28 wherein, said potting material is an epoxy.

30. The standard of claim 28 wherein, said potting material is styrene.

31. A standard for normalizing two or more photodetectors in a single-photon counting system used to measure the luminescence of samples, said standard comprising:

a scintillator whose photon emission has a peak wavelength of about 433 nanometers, said scintillator comprising calcium tungstate:lead, means for exciting said scintillator, said exciting means being either tritium or carbon-14 thymidine, a microplate, means for maintaining said scintillator in said microplate, said means for maintaining said scintillator in said microplate comprising carboxy methyl cellulose, and means for maintaining said scintillator and said means for exciting said scintillator in said microplate, said means for maintaining said scintillator and said means for exciting said scintillator in said microplate comprising an epoxy,

* * * * *